United States Patent
Lawson

Patent Number: 6,074,423
Date of Patent: Jun. 13, 2000

[54] SAFER MORE X-RAY TRANSPARENT SPINAL IMPLANT

[76] Inventor: Kevin Jon Lawson, 2662 Edith Ave., Redding, Calif. 96001

[21] Appl. No.: 09/184,729

[22] Filed: Nov. 2, 1998

[51] Int. Cl.⁷ ...................................................... A61F 2/44
[52] U.S. Cl. ............................................... 623/17; 606/61
[58] Field of Search .......................... 623/17, 16; 606/61, 606/72

[56] References Cited

U.S. PATENT DOCUMENTS

| | | | |
|---|---|---|---|
| 4,011,602 | 3/1977 | Kybicki et al. | 3/1.9 |
| 4,501,269 | 2/1985 | Bagby | 128/92 G |
| 4,834,757 | 5/1989 | Brantigan | 623/17 |
| 5,015,247 | 5/1991 | Michelson | 606/61 |
| 5,015,255 | 5/1991 | Kuslich | 623/17 |
| 5,026,373 | 6/1991 | Ray et al. | 606/61 |
| 5,059,193 | 10/1991 | Kuslich | 606/61 |
| 5,062,845 | 11/1991 | Kuslich et al. | 606/80 |
| 5,263,953 | 11/1993 | Bagby | 606/61 |
| 5,445,639 | 8/1995 | Kuslich et al. | 606/80 |
| 5,458,638 | 10/1995 | Kuslich et al. | 623/17 |
| 5,478,342 | 12/1995 | Kohrs | 606/73 |
| 5,489,307 | 2/1996 | Kuslich et al. | 623/17 |
| 5,489,308 | 2/1996 | Kuslich et al. | 623/17 |
| 5,593,409 | 1/1997 | Michelson | 606/61 |
| 5,609,636 | 3/1997 | Kohrs et al. | 623/17 |
| 5,658,337 | 8/1997 | Kohrs et al. | 623/17 |
| 5,665,122 | 9/1997 | Kambin | 623/17 |
| 5,669,909 | 9/1997 | Zdeblick et al. | 606/61 |
| 5,676,666 | 10/1997 | Oxland et al. | 606/61 |
| 5,700,291 | 12/1997 | Kuslich et al. | 623/17 |
| 5,709,683 | 1/1998 | Bagby | 606/61 |
| 5,720,748 | 2/1998 | Kuslich et al. | 606/80 |
| 5,766,253 | 6/1998 | Brosnahan, III | 623/17 |
| 5,785,710 | 7/1998 | Michelson | 606/61 |
| 5,860,973 | 1/1999 | Michelson | 606/17 |
| 5,876,457 | 3/1999 | Picha et al. | 623/17 |
| 5,906,616 | 5/1999 | Pavlov et al. | 606/61 |

*Primary Examiner*—Bruce E. Snow
*Attorney, Agent, or Firm*—Robert Charles Hill

[57] ABSTRACT

A spine-stabilization implant has a one-piece shell with bone-tapping screw threads on its outside surface. The screw threads are longitudinally interrupted by several end-to-end flutes distributed in parallel around the circumference. Bone-growth access windows are provided at several locations through the flutes. Such construction gives the spine-stabilization implant a hexagonal cross-section with a hollow central core. A drive tool can be slipped into the back end. After spreading two adjacent vertebrae as much as the interconnecting tissues will allow, a bore is made by a surgeon during an operation into the inter-vertebral space of a patient's spine, e.g., deep into the disc. The drive tool is then used to push the spine-stabilization implant down the bore and into the inter-vertebral space. The tool is then twisted such that the bone-tapping screw threads cut into and lock onto the opposite surfaces of the adjacent vertebrae. The tool is then withdrawn. Morselized bone is packed into the spine-stabilization implant to promote new bone growth that will fuse together the opposite surfaces of the adjacent vertebrae.

8 Claims, 3 Drawing Sheets

SAFER MORE X-RAY TRANSPARENT SPINAL IMPLANT

BACKGROUND OF THE INVENTION

1. Field of the Invention

The present invention relates to surgical methods and devices to stabilize vertebra and promote new bone growth that will fuse adjacent stabilized vertebrae, and more particularly to coils or cages that are implanted into full-width bores into the discs of the spine and held in place with screw threads in their outside structures.

2. Description of Related Art

Degenerative disc disease accounts for more than 100,000 low back spinal fusion procedures in the United States annually, according to Columbia Colorado hospitals. The intervertebral disc is a pad of cartilage-type material situated between spinal bones. Each disc serves as a connector, spacer, and shock absorber for the spine. A soft, jelly-like center is contained by outer layers of fibrous tissue. Healthy discs help allow normal turning and bending. Trauma or injury to the spine can cause discs to tear, bulge, herniate, and even rupture. This can be quite painful, as the soft center of the disc leaks, putting pressure on the adjacent nerve roots and spinal cord.

A damaged disc can cause nerve dysfunction and debilitating pain in the back, legs and arms. Typical treatments that provide relief and allow patients to function again include back braces, medical treatment, physical therapy and surgery to remove the disc. A conventional surgical solution removes the bad disc and promotes new bone growth in the space to fuse the adjacent vertebrae together.

Such surgery is very invasive and usually requires two relatively large incisions. One of the incisions is made in the front of the body so the disc can be removed. The second incision is made in the back so connecting rods and anchor screws can be attached to the vertebrae to stabilize them long enough for the new bone to grow. But so much surgical invasion means that the recovery period can take as long as six months.

A recent invention that has been finding favor with orthopedic surgeons is the BAK INTERBODY FUSION SYSTEM by Spine-Tech Inc. (Minneapolis, Minn.). A hollow metal cylinder, or cage, about an inch long, is implanted through a small incision into the spine and into the disc space between two vertebrae. The surgical invasion is highly reduced from the previous method described and patients recover much faster. The disc is not removed whole, it is simply drilled out in two bilateral bores to receive an implant in each bore space between the adjacent vertebrae to stabilize the spine. Morselized bone is harvested from the patient and packed inside the implant. Over time, new bone will fill the inside and outside of the implants and fuse the vertebrae. The degenerated disc need not be separately removed because it is bored out wide enough in the right places and does not block the formation of new bone between two opposite sites on the adjacent vertebrae.

A clinical study on safety and effectiveness involved 947 patients that were submitted to either an anterior or posterior implantation approach. The implantation procedure requires a five-to-six inch incision in the front of the lower abdomen. Portions of disc and bone are drilled out. The BAK implants, comprising hollow threaded titanium cylinders, are screwed into the holes after bone graft is packed inside and then between the implants. Hospitalization time can be as short as three days and patients usually resume their normal activities within three months. In the study, the bone fusion rate was 90.5%, while pain was eliminated or reduced in 85.6% of cases. Functional improvement occurred in 93% of patients. There were no device-related deaths, major paralyses, device failures or deep infections. The results for the entire series showed the duration of surgery was 174 minutes, blood loss averaged 282 cc and the length of hospital stay post operation was 4.4 days. In follow up, 254 patients were evaluated after two years. The BAK device was shown to be successful in 184 patients (72%). In those patients considered successes, the spine had fused, pain was decreased, and there was no loss of muscle strength or function, e.g., the ability to sit, walk, or put on shoes. Complications were comparable to those reported in scientific literature from conventional surgery in which bone alone was used to stabilize and fuse the spine. These complications include damage to the nerve and blood vessels, infection, and the need for additional surgery to further stabilize the spine.

The clinical study was limited to the lower lumbar spine, L2-3, and L5-S1, and involved Grade 1 spondylolisthesis only. The study was limited to patients with one-level or two-level degenerative disc disease, and the researchers did not study patients with significant osteoporosis. In addition, patients with severe psychological and high functional pain were excluded from the study and patients who utilize the technology must otherwise be healthy with no cancer, heart disease or gross obesity. All surgeons in the clinical study were specially trained spinal surgeons. Such special training and specially skilled surgeons were needed because adjacent tissues, especially blood vessels and nerves, can be easily damaged during the procedure. A good deal of force must be applied to sharp, bone-cutting tools during preparation. So a guide tube for the installation tool and implant is used to provide some degree of protection of the adjacent critical tissues.

Most all of the prior art implant devices have substantial short comings, particularly in regard to how the implantation or surgical placement is to be accomplished. The Brantigan-type square cages require hammering the implant device into a prepared bed formed within the disc space. While this is a time-honored technique, it does involve the application by the surgeon of considerable force immediately adjacent to delicate nerve roots and spinal dural tissues.

Two devices recently approved by the FDA and sold commercially, e.g., by Spine-Tech and Surgical Dynamics, are threaded cylindrical devices, usually referred to as "cages". Both appear to perform better than bone graft alone. But these threaded cages have several major difficulties.

First, each implanted cage must be carefully aligned up-and-down in the spine along where the new bone is to grow. Even when properly placed, such implant devices can rotate out of alignment because of their round cross-sections.

Second, the prior art threaded cages all require a separate screw-tapping of the bone with a sharp-edged bone-cutting tool. Such requires much greater care on the part of the operating surgeon to protect nerve tissues and/or blood vessels. Both the Spine-Tech device and the Surgical Dynamics device use bulky working tubes to permit safe use of the sharp-edged bone tap. Placing the working tube safely and properly is the most difficult portion using these surgical devices.

Third, both the FDA-approved cages are made of titanium alloy metal. The titanium's greater x-ray opacity compared to bone makes post-surgical assessment of bone healing across the fusion nearly impossible.

SUMMARY OF THE INVENTION

An object of the present invention is to provide a spine-stabilization device that is safer to surgically implant.

Another object of the present invention is to provide a spine-stabilization implant that allows for x-ray images of new bone growth between adjacent vertebrae to be assessed and tracked over time.

Briefly, a spine-stabilization implant embodiment of the present invention comprises a one-piece bullet-shaped shell with bone-tapping screw threads on its outside surface. The screw threads are longitudinally interrupted by several end-to-end flutes distributed in parallel around the circumference. Bone-growth access windows are provided at several locations through the flutes. Such construction gives the spine-stabilization implant a hexagonal cross-section with a hollow central core. A drive tool is used to twist-in the implant. After spreading two adjacent vertebrae as much as the interconnecting tissues will allow, a bore is made by a surgeon during an operation into the inter-vertebral space of a patient's spine, e.g., deep into the disc. The drive tool is then used to push the spine-stabilization implant down the bore and into the inter-vertebral space. The tool is then twisted such that the bone-tapping screw threads cut into and lock onto the opposite surfaces of the adjacent vertebrae. The tool is then withdrawn. Morselized bone is packed into the spine-stabilization implant to promote new bone growth that will fuse together the opposite surfaces of the adjacent vertebrae.

An advantage of the present invention is that a spine-stabilization implant is provided that encourages bone growth to fuse adjacent vertebrae.

Another advantage of the present invention is that a spine-stabilization implant is provided that is safer to install.

A further advantage of the present invention is that a spine-stabilization implant is provided that improves the x-ray images of the new bone growth so that more accurate assessments of the patient's recovery can be made over time.

The above and still further objects, features, and advantages of the present invention will become apparent upon consideration of the following detailed description of specific embodiments thereof, especially when taken in conjunction with the accompanying drawings.

DETAILED DESCRIPTION OF THE INVENTION

Figure 1:
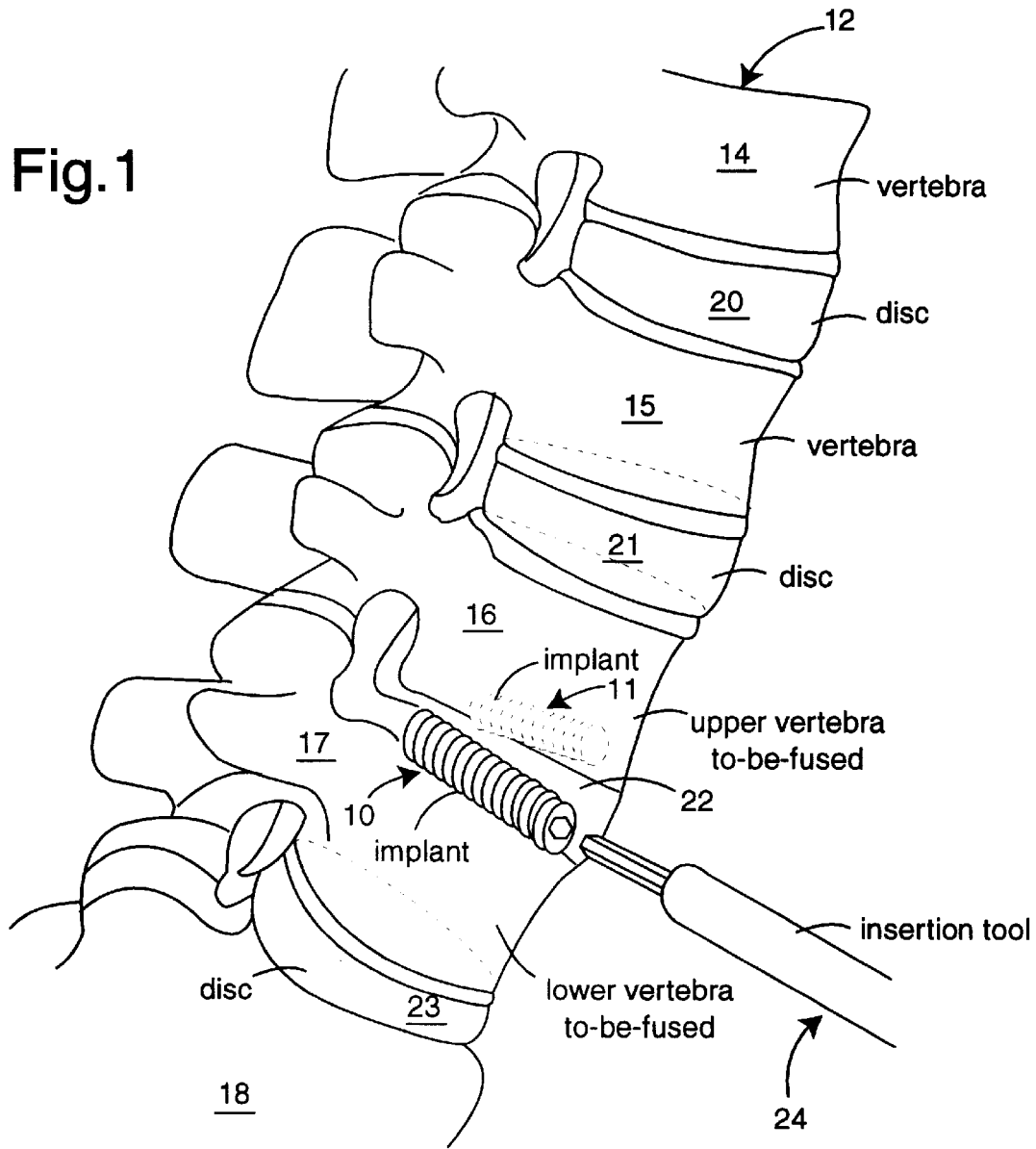
FIG. 1 is a diagram representing the spine of a patient having a spinal implant embodiment of the present invention placed by a surgeon.

FIG. 1 illustrates the placement of a spine-stabilization implant embodiment of the present invention, referred to herein by the reference numeral 10. A second bilaterally placed spine-stabilization implant is referred to herein by the reference numeral 11 and is the same as implant 10. A spine 12 typically comprises a series of vertebrae 14–18 interdigitated with a corresponding series of discs 20–23. Here, disc 22 between vertebra 16 and 17 is assumed to be degenerated. The implants 10 and 11 are surgically placed in the inter-vertebral space between vertebra 16 and 17 with an insertion tool 24. Similar implants are often made of titanium alloy, but less x-ray opaque non-metallic materials are preferred to assist in post-operative follow-ups.

An undersize preparatory bore is made that is large enough in diameter to cut through the cortical bone surfaces of opposite faces of the vertebra 16 and 17 after they have been separated as much as the connecting tissues will allow. Cancellous, or spongy, bone with good blood circulation is thus exposed to the implants 10 and 11. It is important that any remaining disc material be kept out of and away from the bone graft area.

Gary K. Michelson writes in U.S. Pat. No. 5,015,247, issued May 14, 1991, that the fusion rate within the spine is known to be directly related to the amount of exposed vascular bone bed area, the quantity and quality of the fusion mass available, and the extent of stabilization obtained (all other things being constant). The exposure of the vascular bone bed area depends on the size of the preparatory bore that is made for the implant device and also the window connection area that exists between the adjacent vertebrae. The fusion mass depends on what the surgeon packs into the chambers of the implant device and the quantity possible depends on the volume of the chambers within the implant devices. The extent of stabilization obtained depends on how well the implant device fits in the inter-vertebral bore and how well it resists slipping and turning.

The implant devices of the present invention help improve the exposure of the vascular bone bed area by providing several abutting windows to the fusion mass packed within. For example, the fusion mass is morselized bone taken from the patient's hip. The hexagonal cross section helps prevent rotation and the threads prevent the implant device from slipping out the bore hole. Tools of the present invention allow the largest of implant devices to be used in the intervertebral spaces because less margin area with the nerves and dural tissues is needed for the preparatory boring. Therefore no extra space is needed for working tubes or channels.

Figure 2:
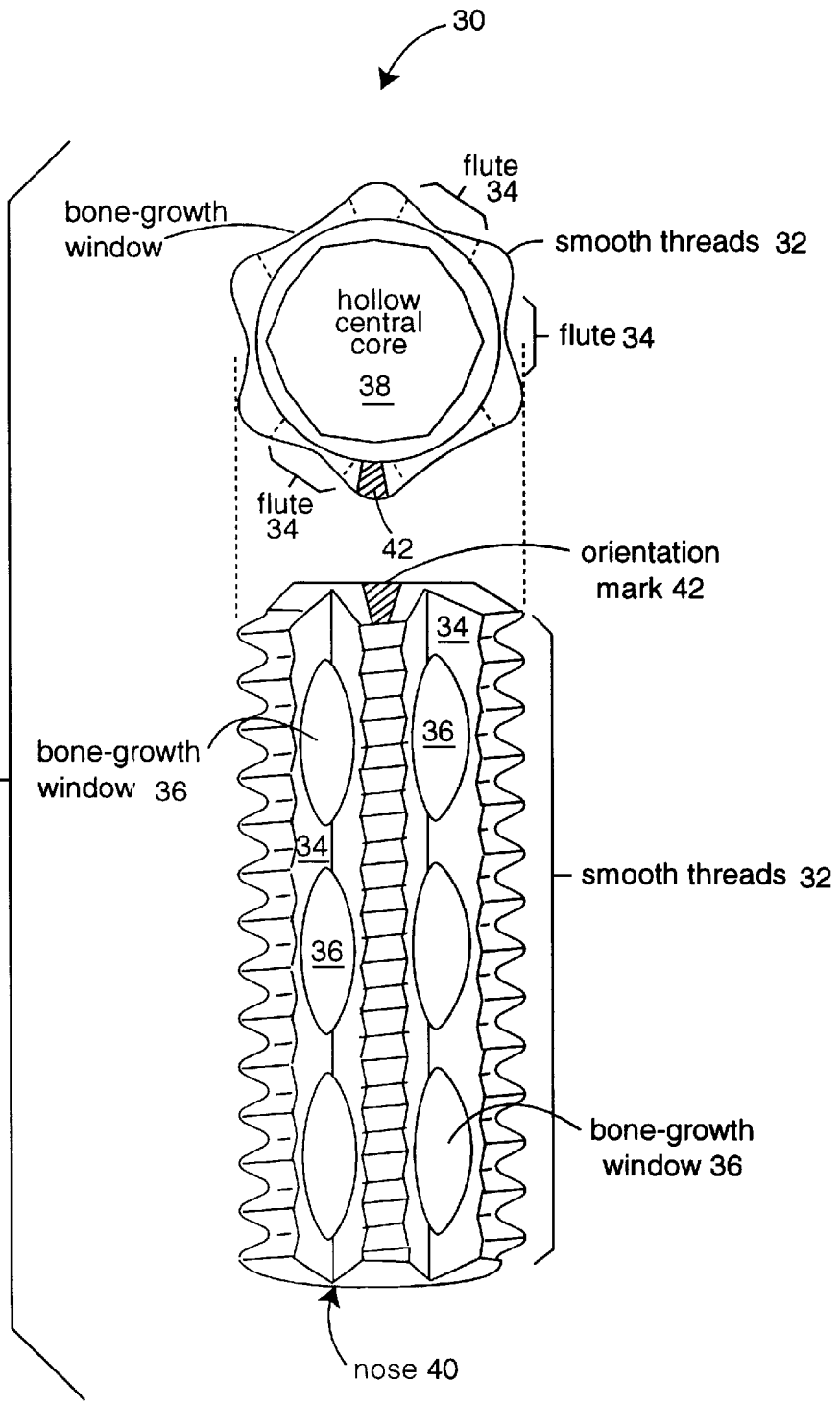
FIG. 2 is an end view over a side view of a stabilization implant embodiment of the present invention similar to that shown in FIG. 1.

FIG. 2 illustrates a spine-stabilization implant 30 which comprises a one-piece bullet-shaped shell with a series of bone-tapping screw threads 32 on its outside surface. The screw threads are longitudinally interrupted by several end-to-end flutes 34 distributed in parallel around the circumference. Bone-growth access windows 36 are provided at several locations through the flutes to a hollow central core 38. The nose 40 can be made rounded and free of threads to help ease the insertion into a bore into the spine. The nose 40 may be made open to allow tissue material to enter the central core 38 during implantation. An orientation mark 42 on the back end helps a surgeon visually determine the up-and-down orientation of the windows 36 even after the implant 30 has been placed in its intended site. It may be advantageous to make such orientation marks stand out in x-ray imaging to help assure the surgeon the implant 30 has maintained its proper orientation long after the surgery.

Although FIG. 2 shows more than one pair of opposite flutes 34 to include bone-growth windows 36, it is preferred that only one such pair exist. Given the strengths of available materials, too many windows 36 in the flutes not aligned up-and-down with the spine after implantation would weaken the whole structure and subject it to crushing. A few such non-aligned windows 36 may be useful for blood circulation, etc.

The described preferred construction gives the spine-stabilization implant a hexagonal cross-section with a hollow central core. A drive tool (FIG. 3) can be slipped into a keyed slot in the hollow core 38. Such a tool would resemble an Allen wrench with a T-handle. After spreading two adjacent vertebrae as much as the interconnecting tissues will allow, a bore is made by a surgeon during an operation into the inter-vertebral space of a patient's spine, e.g., deep into the disc. The drive tool is then used to push the spine-stabilization implant down the bore and into the inter-vertebral space. The tool is then twisted such that the bone-tapping screw threads cut into and lock onto the opposite surfaces of the adjacent vertebrae. The tool is then withdrawn. Morselized bone is packed into the spine-stabilization implant to promote new bone growth that will fuse together the opposite surfaces of the adjacent vertebrae.

The implant device of the present invention and tools of the present invention require no tube protector to keep nerves and dural tissues safe. This allows larger implant devices to be safely placed in a patient's spine while simultaneously reducing the surgical exposure. The prior art typically depends on a cylindrical bone tap with dangerous multiple sharp edges on a threaded cylinder matching the implant cage device.

Figure 3:
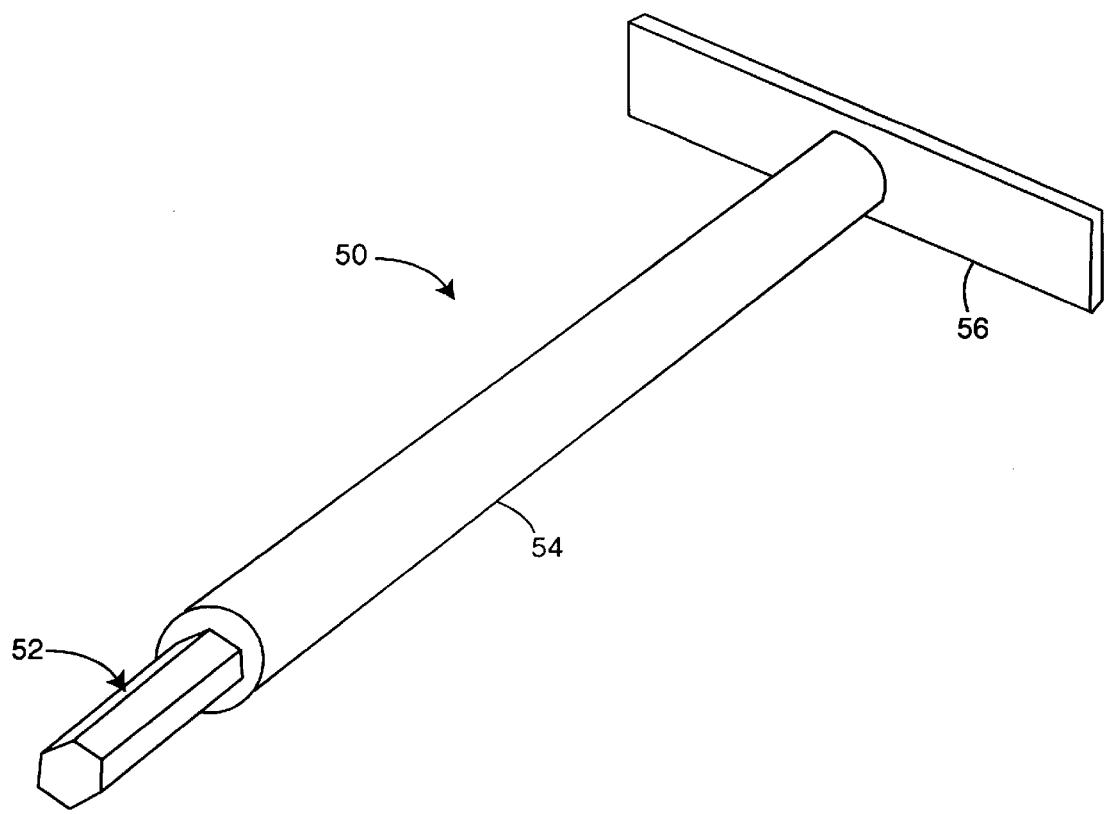
FIG. 3 is a drawing of a tool embodiment of the present invention for placing spinal implant devices in patients during operations.

FIG. 3 illustrates a tool embodiment of the present invention, referred to herein by the general reference numeral 50. The tool 50 includes a keyed drive end 52 that can be hexagonal like an Allen wrench, square like a socket wrench, or bladed like a screwdriver. A smooth shaft 54 connects this to a T-handle 56 that is twisted by the surgeon to install the implant between adjacent vertebrae. Tool embodiments of the present invention can be used with conventional implant cages to implant them through substantially smaller surgical exposures for improved safety.

Implant devices of the present invention make their own receiving threads as they are advanced into the surgical bore in the spine. Prior art devices assume that the bone is very hard and very sharp tools are necessary to machine it to proper shape. In fact, once a circular bed or channel has been prepared into the disc space, the vertebral-end-plate bone (cancellous bone) is rarely very tough or hard.

The self-taping threads need not have an aggressive sharp-cutting edge in lateral cross-section, but rather rounded or truncated threads. A modified helical shape is preferred that gives adequate purchase and that can cut threads into bone while at the same time being benign, or harmless, to nerves and other sensitive soft tissues.

The implant device of the present invention is slightly bullet shaped, or smaller diameter at the forward edge where it initially engages into the bone, and has somewhat flat end or edge surfaces where bone-growth windows are located. While this is a device that screws into the inter-vertebral space it is not a cylindrical shape nor is it a simple "tap" shape. In particular embodiments of the present invention, the structure has a hexagonal cross-section with the threads forming rounded outside points and longitudinal flutes form concave outside flats between.

In alternative embodiments of the present invention, the implant devices are made out of an ultrahigh molecular weight polyethylene, or other biocompatible, nonmetallic material which is relatively translucent to x-rays. For example, alumina, foamed alumina, other ceramics, or even aerogel may be used. Implant devices that are almost transparent to x-ray would allow better x-ray assessment of the bone-graft and healing of fusion following cage placement. Similarly, it may be advantageous to use materials with responses substantially different from bone for CAT and MRI imaging.

Alternative embodiments of the present invention may also be coated with inorganic compounds or proteins that stimulate or seed the formation of bone across their surfaces. In some cases it may be advantageous to provide piping for blood flow though the chambers of the implant device that communicate with the vascular bone to be fused.

Although particular embodiments of the present invention have been described and illustrated, such is not intended to limit the invention. Modifications and changes will no doubt become apparent to those skilled in the art, and it is intended that the invention only be limited by the scope of the appended claims.

The invention claimed is:

1. A spine-stabilization implant, comprising:
   a one-piece shell having a hexagonal cross-section;
   a series of bone-tapping screw threads on an outside surface of the shell;
   a series of flutes longitudinally oriented and in parallel around the outside circumference of the shell and that interrupt the screw threads and that allow material cut by the screw threads to accumulate;
   said threads forming rounded outside points and said flutes forming concave outside flats;
   a plurality of bone-growth access windows provided at several locations through at least one opposite pair of flutes; and
   a hollow central core connected to each of the bone-growth access windows and providing a space for packing with materials to promote bone growth through the shell and opposite sided bone-growth access windows between adjacent bones contacted by said outside circumference of the shell.

2. The spine-stabilization implant of claim 1, wherein:
   the shell includes a rounded nose providing for easier insertion of the spine-stabilization implant down a bore that is made by a surgeon during an operation into the inter-vertebral space of a patient's spine.

3. The spine-stabilization implant of claim 1, wherein:
   the series of bone-tapping screw threads and the flutes provide for a self-tapping and complete locking into opposite surfaces of adjacent vertebrae.

4. The spine-stabilization implant of claim 1, further comprising:
   a back end of the shell for receiving a drive tool that allows a surgeon to push the shell into inter-vertebral space of a patient's spine, and then to twist the threads into opposite surfaces of adjacent vertebrae, and then to withdraw the tool straight out.

5. The spine-stabilization implant of claim 1, wherein:
   the shell comprises a material with an x-ray opacity substantially less than that of bone and that provides less of an obstacle than solid titanium to clear x-ray imaging of any new bone growth that may occur through the central core or the bone-growth windows after being surgically implanted in a patient.

6. The spine-stabilization implant of claim 1, wherein:
   the shell has a rounded nose which is closed and thus stops tissues from entering the central core during insertion into a patient's body; and the series of bone-tapping screw threads are smoothed down and diminish as they move forward on said rounded nose.

7. The spine-stabilization implant of claim 1, wherein:

an orientation mark on a back end of the shell informs a surgeon what the orientation of the implant is relative to a patient's spine after implantation.

8. A spinal-implant device for stabilizing vertebrae long enough to generate new bone growth between adjacent vertebra, comprising:

a one-piece shell having a hexagonal cross-section;

a series of bone-tapping threads on an outside surface of the shell and sharp enough only to provide for self-tapping into cancellous bone and not sharp enough to cut nerve and dural tissues;

a series of flutes longitudinally oriented and in parallel around the outside circumference of the shell and that interrupt the threads;

said threads forming rounded outside points and said flutes forming concave outside flats;

a plurality of bone-growth access windows provided at several locations through at least one opposite pair of flutes; and a hollow central core connected to each of the bone-growth access windows and providing a space for packing with materials to promote bone growth through the shell and opposite sided bone-growth access windows between adjacent bones contacted by said outside circumference of the shell.

* * * * *